(12) United States Patent
Fullerton

(10) Patent No.: US 9,204,985 B1
(45) Date of Patent: Dec. 8, 2015

(54) COMPRESSION LEG SUPPORT (71) Applicant: M. J. Fullerton, Pryor, OK (US)

(72) Inventor: M. J. Fullerton, Pryor, OK (US)

( * ) Notice: Subject to any disclaimer, the term of this patent is extended or adjusted under 35 U.S.C. 154(b) by 0 days.

(21) Appl. No.: 14/546,191

(22) Filed: Nov. 18, 2014

(51) Int. Cl.
*A61F 5/01* (2006.01)

(52) U.S. Cl.
CPC ............... *A61F 5/0104* (2013.01); *A61F 5/01* (2013.01); *A61F 5/0102* (2013.01); *A61F 5/0106* (2013.01)

(58) Field of Classification Search
CPC ...................................................... A61F 5/0104
USPC ............ 5/600, 621, 624; 128/846, 869, 882, 128/878, 879; 602/26, 27, 24, 21, 62, 63, 602/61
See application file for complete search history.

(56) References Cited

U.S. PATENT DOCUMENTS

| | | | |
|---|---|---|---|
| 1,226,013 A | 5/1917 | Roth | |
| 1,663,921 A | 3/1928 | Pierce | |
| 2,413,053 A | 12/1946 | Kolarik | |
| 2,522,853 A | 9/1950 | Black | |
| 2,558,986 A | 7/1951 | Seelert | |
| 2,632,440 A * | 3/1953 | Hauser et al. | 602/16 |
| 2,943,622 A | 7/1960 | Nelson | |
| 4,688,559 A | 8/1987 | Vito et al. | |
| 5,490,831 A | 2/1996 | Myers et al. | |
| 6,024,713 A * | 2/2000 | Barney | 602/23 |
| 6,960,175 B1 | 11/2005 | Myers | |
| 7,393,335 B2 | 7/2008 | Carvey et al. | |
| 7,806,842 B2 * | 10/2010 | Stevenson et al. | 602/26 |
| 7,815,586 B2 * | 10/2010 | Grant et al. | 602/23 |
| 7,918,812 B2 | 4/2011 | Knecht | |
| 8,679,046 B2 | 3/2014 | Ital et al. | |

\* cited by examiner

*Primary Examiner* — Michael Brown
*Assistant Examiner* — Tarla Patel
(74) *Attorney, Agent, or Firm* — Head, Johnson & Kachigian, P.C.

(57) ABSTRACT

A leg support that attaches to a user's upper leg and extends below the user's foot, where stepping on the portion below the user's foot causes the portion around the user's upper leg to tighten. This allows the leg support and the user's upper leg to bear the user's weight with the user's foot remaining untouched. When the user takes his or her weight off of the leg support, the portion around the user's upper leg loosens for the user's comfort. The leg support insures that there is zero pressure on the bottom of the user's foot and all of the user's weight and vertical shear pressure is converted into horizontal compression pressure around the user's thigh, while the user's center of gravity remains in a position that allows upright balance to be maintained.

14 Claims, 8 Drawing Sheets

COMPRESSION LEG SUPPORT

CROSS REFERENCE

Not Applicable.

BACKGROUND OF THE INVENTION

1. Field of the Invention

This invention relates generally to a leg support, and more particularly, but not by way of limitation, to a leg support that allows a user to walk without putting any pressure on the user's foot by transforming a portion of the vertical shear force to horizontal compressive force around the user's upper leg.

2. Description of the Related Art

There are many circumstances that require a person to keep all pressure off his or her foot or lower leg, including broken bones, sprains, tears, cuts, bruises, abrasions, burns, and injuries due to diabetes. Typically, this necessitates the use of crutches or a wheelchair, both of which are cumbersome and limit the mobility of the user. Many people in such circumstances opt for a device that allows them to continue walking, such as a boot or other device designed to minimize the impact on the injured area. These devices do not completely relieve the pressure on the injured area, however, potentially prolonging recovery time and increasing the user's pain.

For example, diabetes can cause a variety of injuries to a person's foot, including ulcers. The standard treatment for a foot ulcer is a boot with a pad surrounding the ulcer, with an opening cut into the pad at the location of the ulcer to prevent impact to the ulcer itself. Every step, however, impacts the skin adjacent the ulcer, pulling the healing tissue. This is not only painful, but also delays healing. Unhealed ulcers can lead to amputation. The best course of treatment is to keep any and all pressure from the entire foot, but many people do not want or cannot tolerate the resultant disruption to their lives caused by such lack of mobility.

A further consideration is that a person's knee needs to bend to allow the person to sit or stand without assistance. May braces, however, are rigid at the knee and do not provide for bending. Getting up from a seated position is very difficult, if not impossible, with a rigid, straight leg brace.

Based on the foregoing, it is desirable to provide a leg support that transfers all of the pressure of walking to the upper leg rather than the lower leg or foot.

It is further desirable for such a leg support to allow a user to walk without putting any pressure on the user's foot.

It is further desirable for such a leg support not to touch a user's foot at all.

It is further desirable for a user to be able to take such a leg support off and on without having to insert his or her foot through any openings.

It is further desirable for such a leg brace to bend at the knee to allow a user to get up from a seated position.

It is further desirable to allow the user to finely adjust the pressure of the leg support to maximize comfort and pressure for all positions: standing, seated, ad walking. It is desirable for the user to have total control of the pressure of the leg support on the user's leg. It is further desirable for such a leg brace to allow small adjustments and to hold those adjustments without constant readjustment as the leg support is used.

It is further desirable for such a leg support to have a knee hinge that bends in an arch rather than at a 90° angle.

It is further desirable for the knee hinge of the leg support to bend or flex in only one plane or direction.

It is further desirable for such a leg support to provide confidence in a user to facilitate increased usage.

It is further desirable for such a leg support to be simple and consistent in usage in design, allowing for mass production and affording removal of leg pain and pressure on leg, knee, ankle, foot, and sole of foot without major cost of production.

It is further desirable for such a leg support to allow a user to put the leg support on and take the leg support off easily and to quickly and accurately adjust all pressure and clearance of the sole of the foot.

SUMMARY OF THE INVENTION

In general, in a first aspect, the invention relates to a leg support comprising an upper assembly capable of surrounding the user's upper leg, where the upper assembly has an adjustable circumference; and a rod attached to the upper assembly such that moving the rod upward causes the circumference of the upper assembly to decrease. The rod is sufficiently long to extend from the upper assembly past the user's foot such that when the user takes a step on a walking surface, the rod strikes the walking surface and causes the circumference of the upper assembly to decrease, preventing the user's foot from striking the walking surface.

The upper assembly may comprise a wrap and a wire assembly, where the rod is attached to the wire assembly. The wrap may comprise a front section, a back section, and two side sections, where the two side sections each have a double layer such that a portion of the front section and a portion of the back section fit between the layers of the side sections to form a cylinder with an adjustable circumference. The wire assembly may comprise a first closure side, a second closure side removably attached to the first closure side, and at least one wire extending between the first closure side and the second closure side, such that the first closure side, the second closure side, and the at least one wire surround the wrap. The first closure side may be attached to the wrap. The first and second closure sides may each have a series of posts. The first end of the wire may be attached to the first closure, the wire may alternately wrap around the posts of the second closure side and the posts of the first closure side in series, and the second end of the wire may be attached to the second closure. The wire assembly may further comprise a tensioning device.

The rod may have at least one channel through which the at least one wire extends. The upper assembly may further comprise two anchor bars, where the anchor bars are attached to the wrap. The anchor bars may each have at least one channel through which the at least one wire extends. The rod may be located between the two anchor bars with the channels of the rod aligning with the channels of the anchor bars, such that the wire extends through one of the channels in one of the anchor bars, through one of the channels in the rod, then through one of the channels in the other anchor bar.

The leg support may further comprise two bars attached to the upper assembly and extending downward, where the bars are sufficiently long to extend from the upper assembly past the user's foot but not as long as the rod. One of the bars may run along the inside of the user's leg, while the other bar and the rod run along the outside of the user's leg. The leg support may further comprise a cross piece connecting the two bars under, but not touching, the user's foot. A flat piece may be attached to the rod such that pressing the bottom of the flat piece causes the rod to move upward. The flat piece may be connected to the cross piece via two u-shaped connectors, where the u-shaped connectors are attached to the flat piece and extend over the cross piece such that the flat piece cannot move substantially laterally but may move vertically relative to the cross piece.

The bars may each comprise an upper bar, a lower bar, and a middle piece located between the upper bar and lower bar, where the middle piece is located adjacent the user's knee when the leg support is in use. Each of the bars may further comprise a connector plate pivotally connected to the upper bar, the lower bar, and the middle piece such that bar hinges during use. The leg support may further comprise a strap securing the two bars to the user's lower leg. The rod may comprise an upper rod, a lower rod, and a spring connecting the upper rod and the lower rod, where the spring is located adjacent the user's knee when the leg support is in use.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

Figure 1:
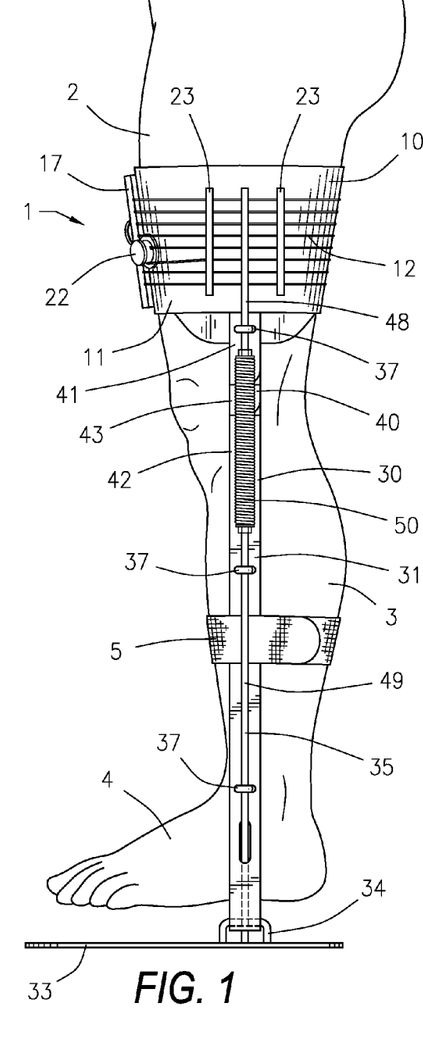
FIG. 1 is a side view of the compression leg support in place on a user's leg, with the compression leg support in a non-compressed position.
Figure 2:
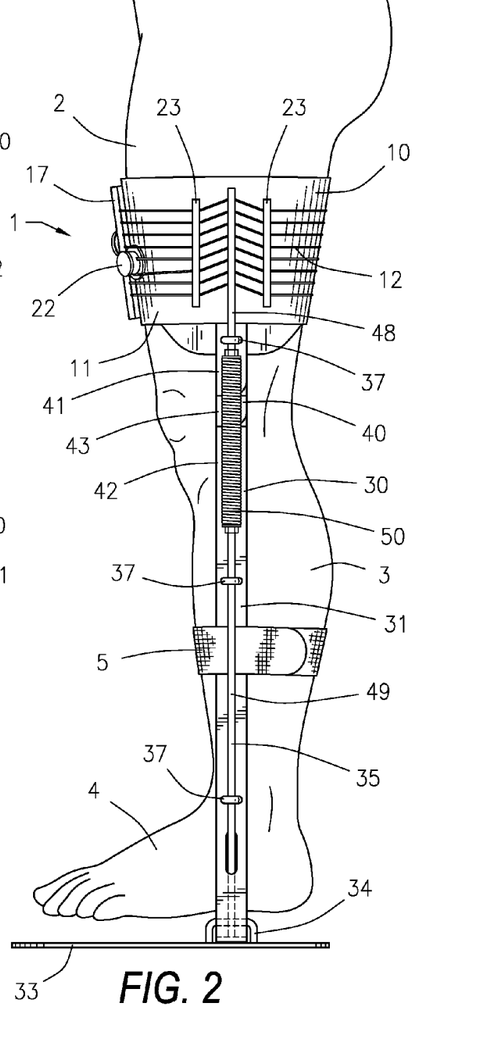
FIG. 2 is a side view of the compression leg support in place on a user's leg, with the compression leg support in a compressed position.
Figure 3:
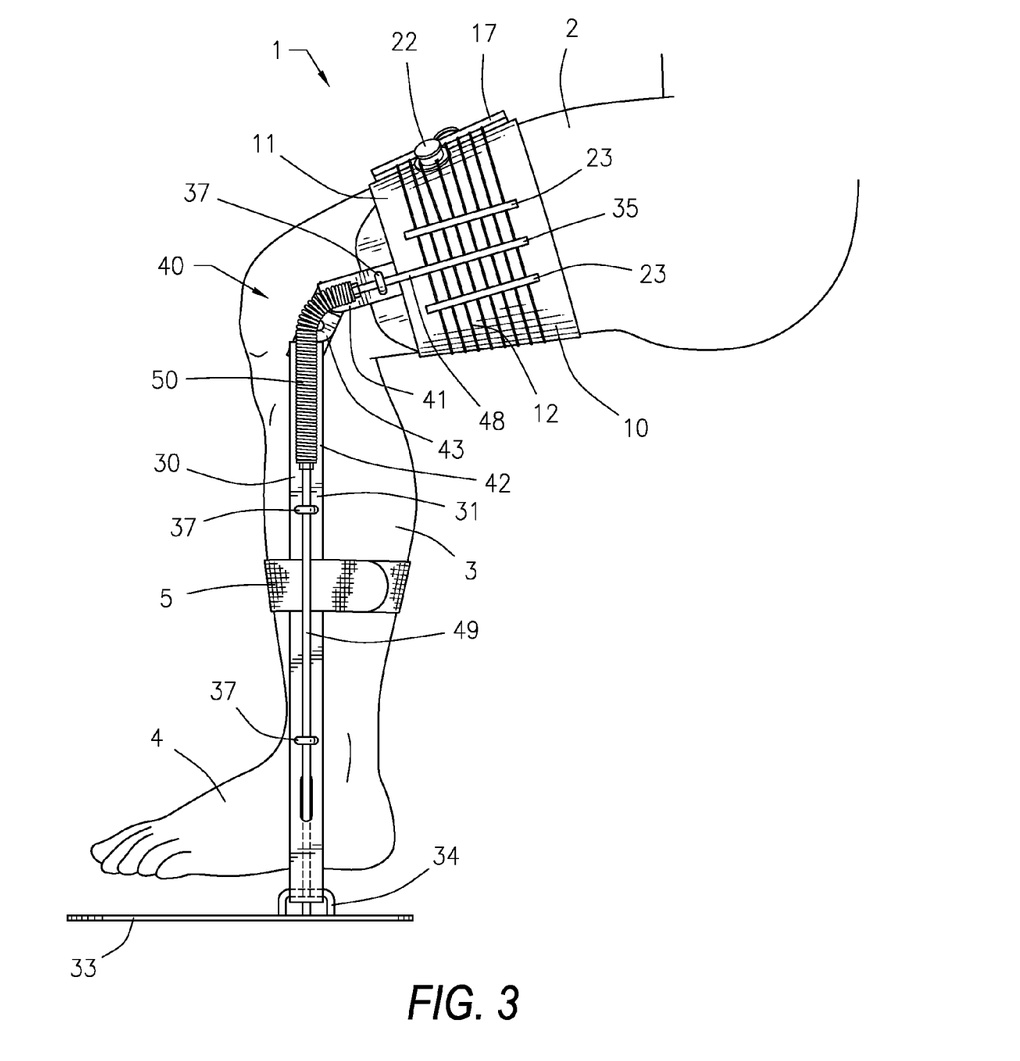
FIG. 3 is a side view of the compression leg support in place on a user's leg, with the compression leg support in a bent position.
Figure 4:
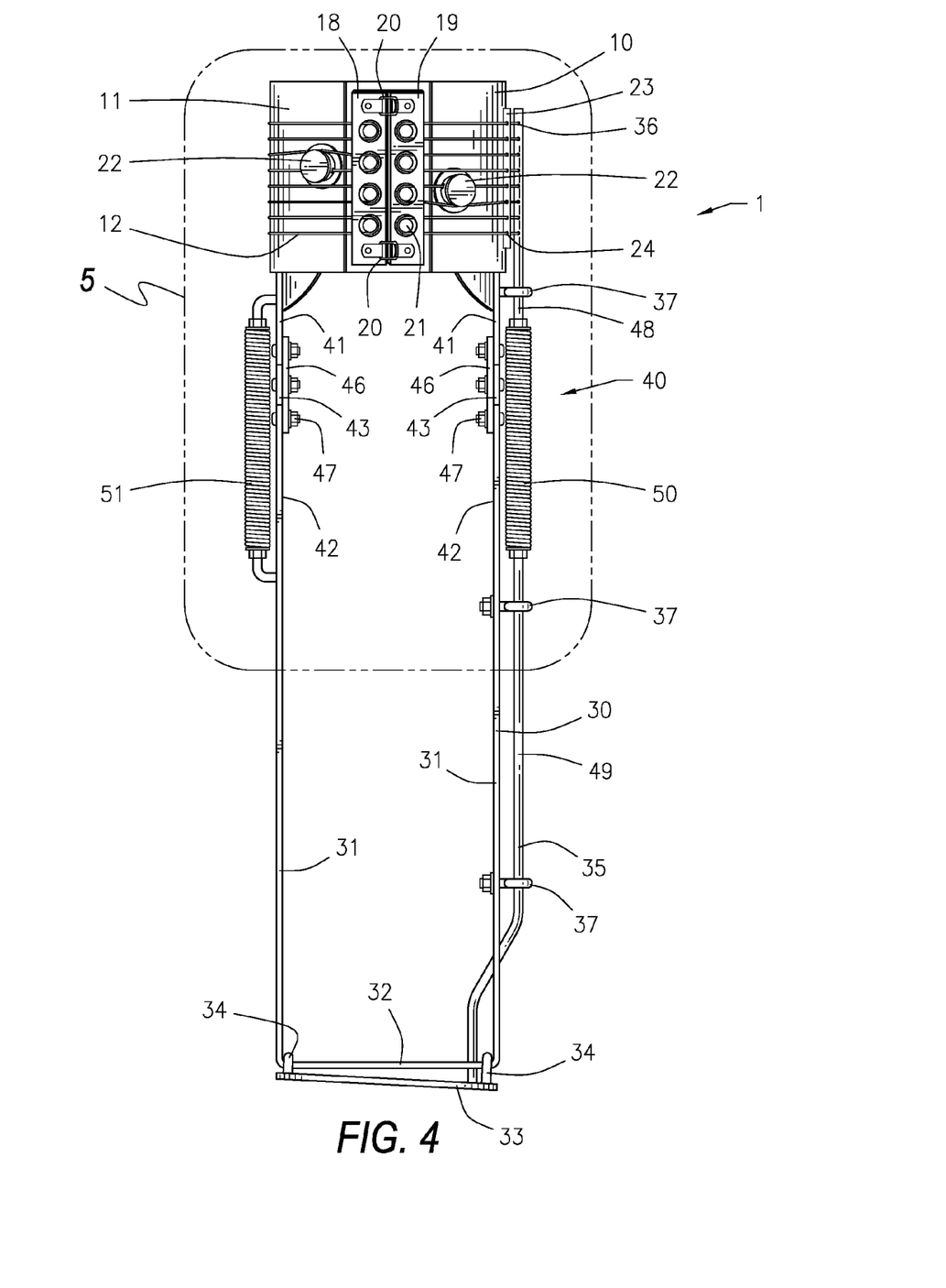
FIG. 4 is front view of the compression leg support in a non-compressed position.
Figure 5:
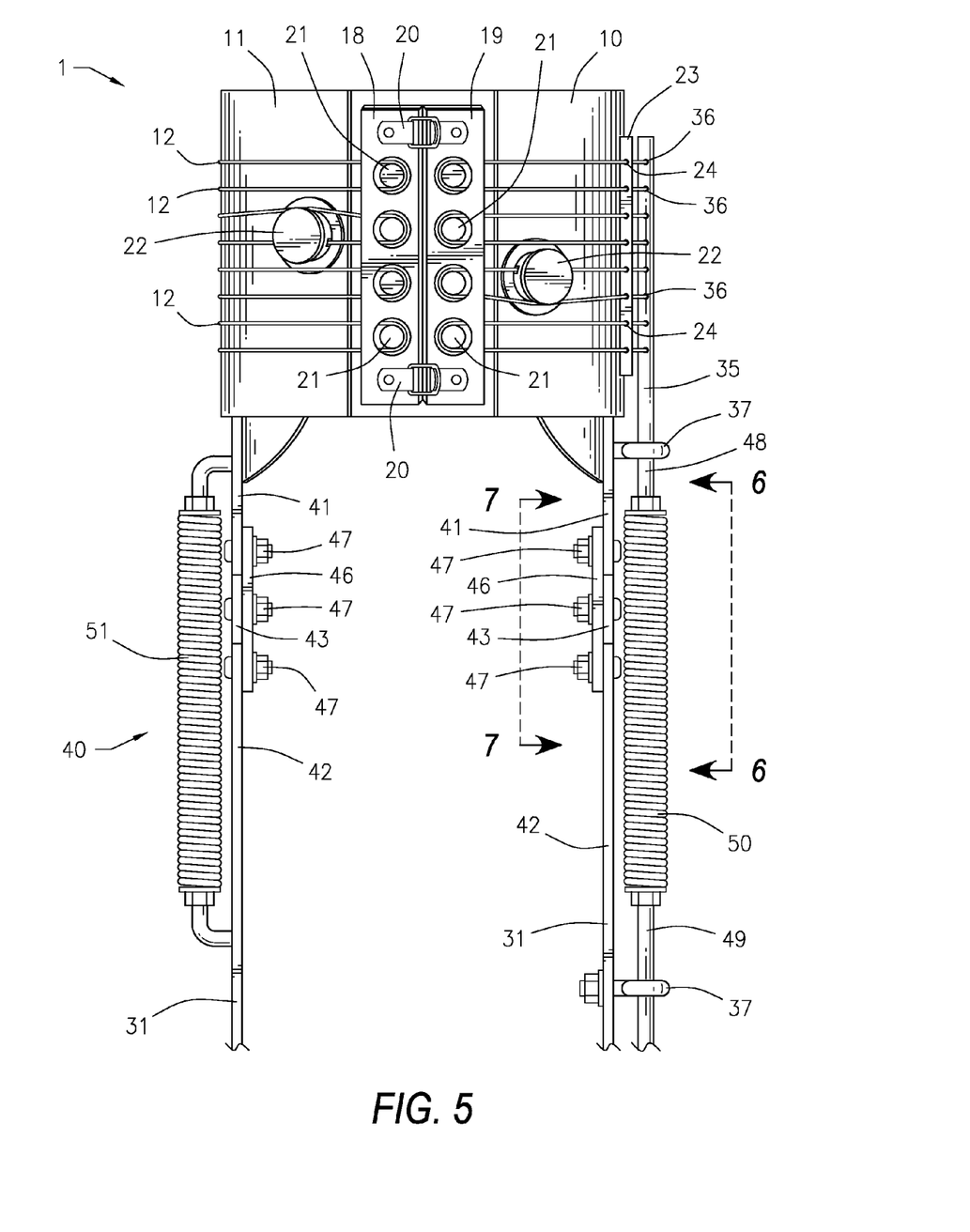
FIG. 5 is a close-up front view of the upper portion of the compression leg support in a non-compressed position.

In general, in a first aspect, the invention relates to a leg support 1. The leg support 1 may wrap around a user's upper leg 2, as shown in FIGS. 1 through 3. The leg support 1 may surround the user's lower leg 3 and foot 4. The leg support 1 may optionally have a strap 5 that secures the leg support 1 to the user's lower leg 3. The strap 5 may allow the user to control their center of gravity within the leg support 1 by moving their lower leg 3 forward or backward in the leg support 1. Alternately, the user may use the leg support 1 without the strap 5 if desired. The leg support 1 may not touch the user's foot 4, either when the user has his or her weight on his or her leg or not.

The leg support 1 may comprise an upper assembly 10, which surrounds the user's upper leg 2 when in use, and a bar and rod assembly 30, which extends from the upper assembly 10 to beyond the user's foot 4 when in use. During use, the user may secure the upper assembly 10 around the user's upper leg 2 at a comfortable tension. The user may take a step, shifting his or her weight to the leg support 1. As the bar and rod assembly 30 extends beyond the user's foot 4, the bar and rod assembly 30 may come into contact with the floor before the user's foot 4. As a result of coming into contact with the floor, the bar and rod assembly 30 may cause the upper assembly 10 to tighten around the user's upper leg 2, as described below. Thus, a portion of the vertical shear pressure from the step may be transferred into horizontal compressional force around the user's upper leg 2, essentially causing the user's upper leg 2 to bear the user's weight, while the remainder of the vertical force is used to support in the thigh in an upward direction. The increased compressive force may prevent the upper assembly 10 from slipping on the user's upper leg 2 and may keep the user's foot 4 from ever coming into contact with either the floor or the leg support 1. The result of this unique design may be zero pressure on the sole of the user's foot.

Figure 8:
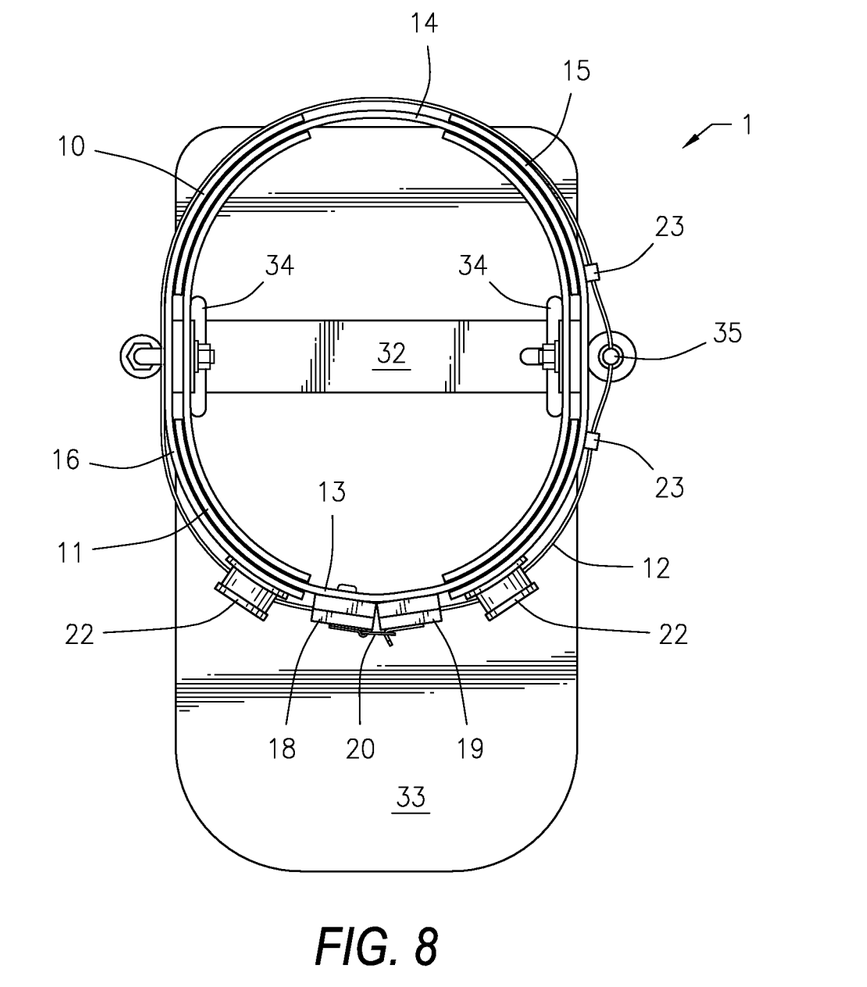
FIG. 8 is a top view of the compression leg support.
Figure 9:
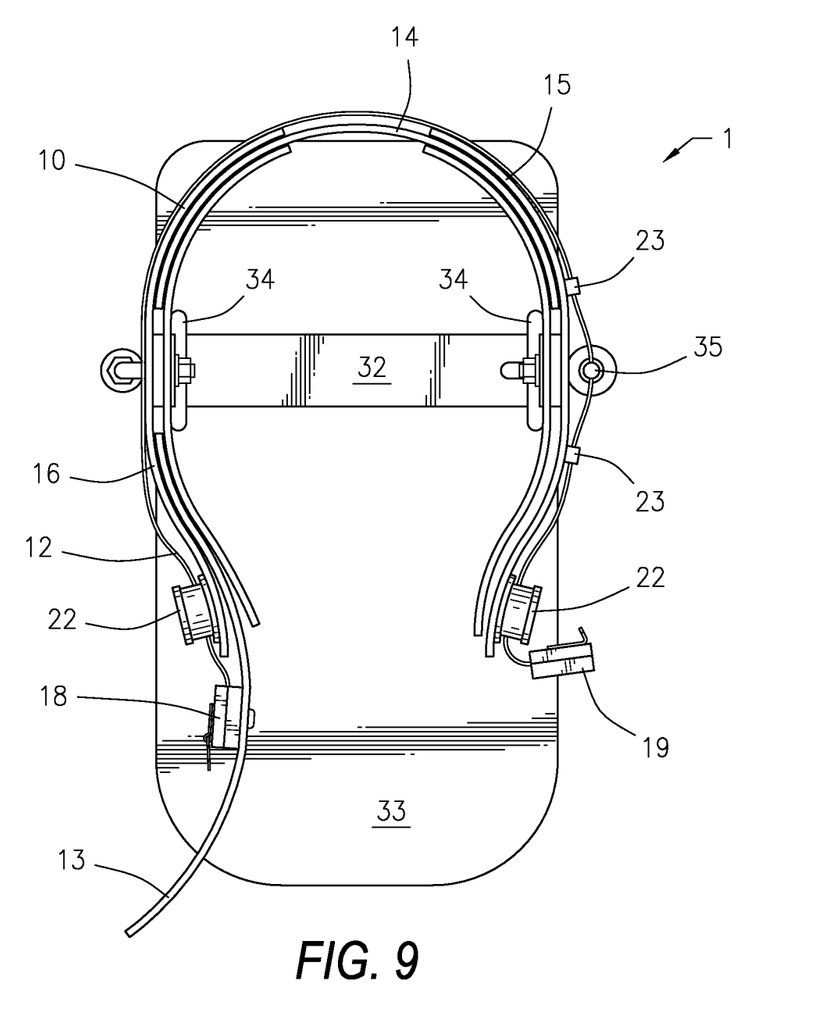
FIG. 9 is a top view of the compression leg support in an open position.
Figure 10:
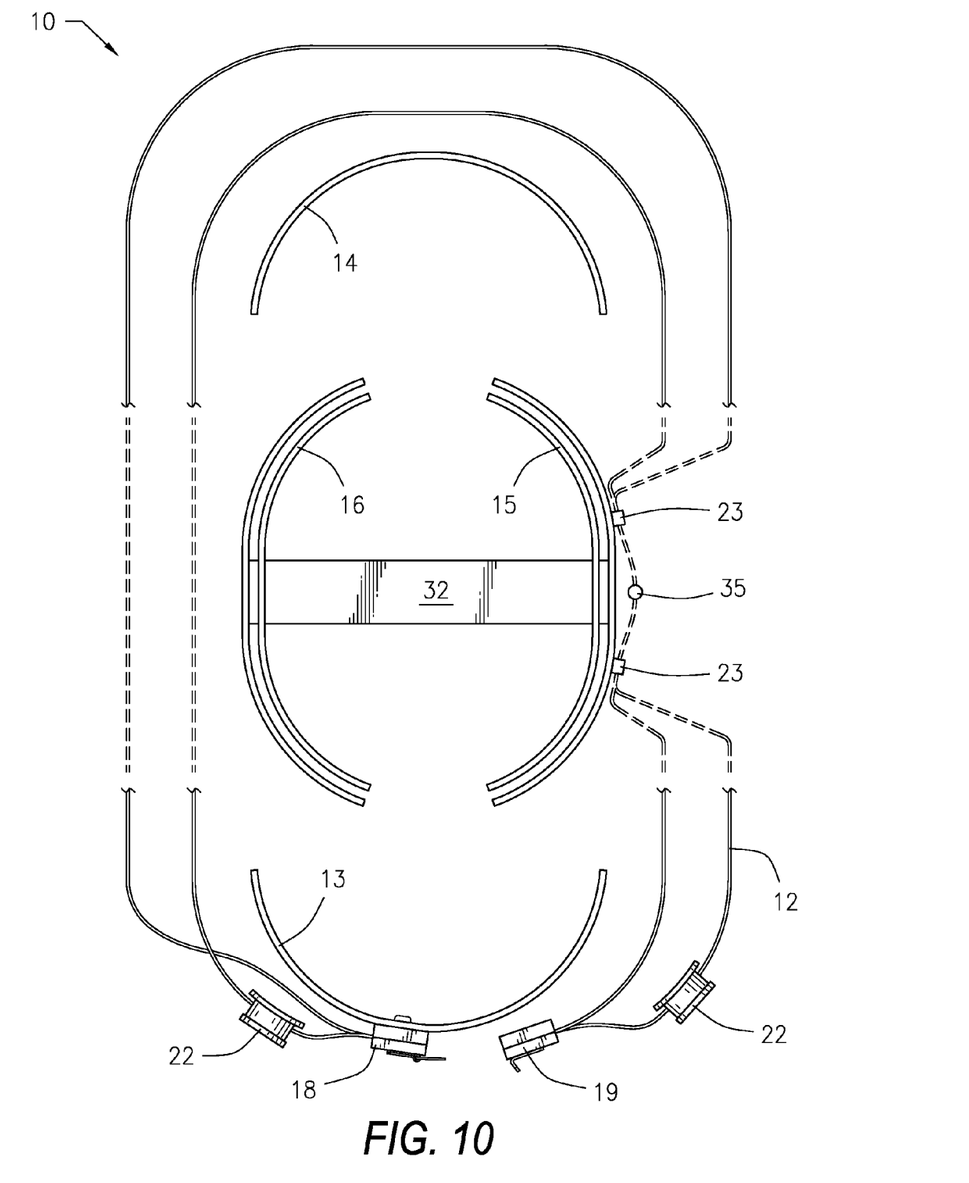
FIG. 10 is an exploded top view of the compression leg support in an open position.

The upper assembly 10 may comprise a wrap 11 and at least one wire 12 substantially encircling the wrap 11. The wrap 11 may be formed in such a way that it may tighten and loosen repeatedly during use without bunching. For example, as shown in FIGS. 8, 9, and 10, the wrap 11 may comprise a front section 13, a back section 14, a side section 15, and an opposing side section 16. The side sections 15 and 16 may each have a double layer, such that the sides of the front and back sections 13 and 14 may fit between the layers of the side sections 15 and 16 to form a cylinder. The cylinder may have a larger or smaller diameter depending on how much of the sections 13, 14, 15, and 16 overlap.

The wires 12 may fully encircle the wrap 11, which necessitates the user slipping the entire upper assembly 10 over his or her foot 4 and sliding it up into place on his or her upper leg 2 for use. Alternately, as shown in the drawings, the wires 12 may attach to a closure device 17, allowing the upper assembly 10 to be opened, placed around the user's upper leg 2, and closed for use. The closure device 17 may comprise a first closure side 18, which may attach to the front section 13 of the wrap 11, and a second closure side 19, which may be secured to the first closure side 18, such as via one or more attachment devices 20. The attachment devices 20 may be any desired attachment devices. The upper assembly 10 may open completely to go around the user's thigh and may close completely to allow pressure adjustment. The design of the upper assembly 10 may allow pressure to be totally uniformly distributed around the user's thigh with no one pressure point causing pain and discomfort.

The wire 12 may attach to both the first closure side 18 and the second closure side 19 such that the wire 12 extending between the first closure side 18 and the second closure side 19 may surround the wrap 11. The wire 12 may attach to the closure 17 in such a way that its tension may be adjusted. For example, the first closure side 18 and the second closure side 19 may each have a series of posts 21. A single wire 12 may be secured at one end to the first closure side 18 and may then extend to the second closure side 19, where it wraps around one of the posts 21. It may then extend back to the first closure side 18, where it wraps around another of the posts 21. It may extend backward and forward between the first and second closure sides 18 and 19 repeatedly before finally securing at its second end to the second closure side 19. A tensioning device 22 may be attached to the wire 12 such that tightening the tensioning device 22 may cause the wire 12 to slide along the posts 21, decreasing the circumference of the circle formed by the wire 12 and closure device 17. Loosening the tensioning device 22 may produce the opposite effect, assuming the tensioning device 22 was previously tightened such that there is slack wire 12 available. Alternately, multiple wires 12 and multiple tensioning devices 22 may be used. The use of multiple layers of wire 12 may allow a small vertical movement to translate to a large horizontal compression. For example, ½ inch vertical movement of the rod may equal approximately 2 inches of compression of the horizontal components.

The wires 12 may extend through two anchor bars 23, both of which may be attached to one of the side sections 15 or 16 of the wrap 11, depending on whether the leg support 1 will be used on the right or left leg. Preferably, the anchor bars 23 may be attached on the side section 15 or 16 that is on the outer side of the user's leg, as opposed to the side adjacent the user's other leg. This is for the comfort of the user. The anchor bars 23 may be attached to the side section 15 or 16 such that they do not move relative to the side section 15 or 16, while the wire 12 may travel through channels 24 in the anchor bars 23 such that they may freely move laterally through the anchor bars 23 but may not move vertically.

The bar and rod assembly 30 may comprise two bars 31 extending downward from the upper assembly 20. One bar 31 may extend downward from each of the side sections 15 and 16 of the upper assembly 20. The bars 31 may be joined at their bottoms by a cross piece 32 extending therebetween. The bars 31 may be sufficiently long that the cross piece 32 is located below, but not touching, the user's foot 4 when the leg support 1 is in use. A flat piece 33 may be connected to the cross piece 32 in such a way that the distance between at least one side of the flat piece 33 and the cross piece 32 is variable. For example, as shown in the drawings, the flat piece 33 may be connected to the cross piece 32 via two u-shaped connectors 34. The u-shaped connectors 34 may be secured to the flat piece 33 such that they extend over the cross piece 32 adjacent the bars 31. Thus, the flat piece 33 is prevented from moving laterally relative to the cross piece 32. One of the u-shaped connectors 34 may be short, such that it allows minimal vertical movement of the flat piece 33 relative to the cross piece 32. The other u-shaped connector 34 may be long, such that it allows greater vertical movement of the flat piece 33 relative to the cross piece 32. Alternately, both u-shaped connectors 34 may be long enough to allow vertical motion of the flat piece 33 relative to the cross piece 32. The flat piece 33 may be generally rectangular as shown, foot-shaped, or any other desired shape and may be large enough to cover the bottom of the user's foot 4, as shown, or any other desired size.

A rod 35 may be attached to the flat piece 33 on the side with the long u-shaped connector 34, and may extend upward along one of the bars 31 and between the two anchor bars 23. The rod 35 may have a plurality of channels 36 corresponding to the channels 24 in the anchor bars 23. The wire 12 may travel through the channels 36. Thus, when the user takes a step, the flat piece 33 may come into contact with the ground, forcing the flat piece 33 upward relative to the cross piece 32 on the side with the long u-shaped connector 34. This may cause the rod 35 to move upward relative to the cross piece 32, and consequently relative to the bars 31 and the upper assembly 10, as they are all connected. The rod 35 may be held in place laterally relative to the bar 31 by one or more eyelets 37.

The upward motion of the rod 35 may cause the wire 12 to be moved upward vertically at all of the points at which it extends through the channels 36 in the rod 35. This vertical motion of the wire 12 may be limited to the area between the two anchor bars 23, as they are secured to the wrap 11. This vertical motion may cause the wire 12 to tighten around the wrap 11. The more times the wire 12 extends substantially around the wrap 11, the greater the distribution of compressive force caused by the vertical motion of the rod 35. Thus, taking a step causes the upper assembly 10 to tighten around the upper leg 2 of the user, allowing the user's upper leg 2 to bear the user's weight rather than the user's lower leg 3 or foot 4.

When the user shifts his or her weight to the opposite foot, the pressure may be taken off the flat piece 33, allowing the rod 35 and consequently the wire 12 to return to their normal positions. This increases the circumference of the upper assembly 10. This allows the upper assembly 10 to be tight enough to be effective when needed, but loose enough to be comfortable when not needed. The process repeats with each step.

Figure 6A:
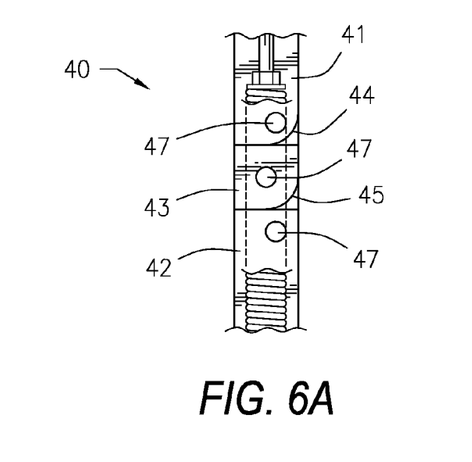
FIG. 6A is a close-up side view of the outside of the hinge assembly.
Figure 6B:
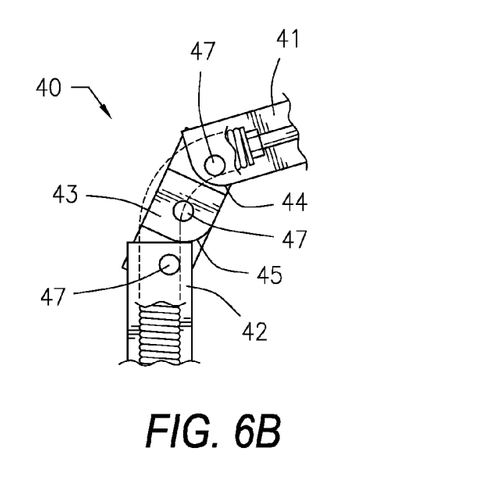
FIG. 6B is a close-up side view of the outside of the hinge assembly in a bent position.
Figure 7A:
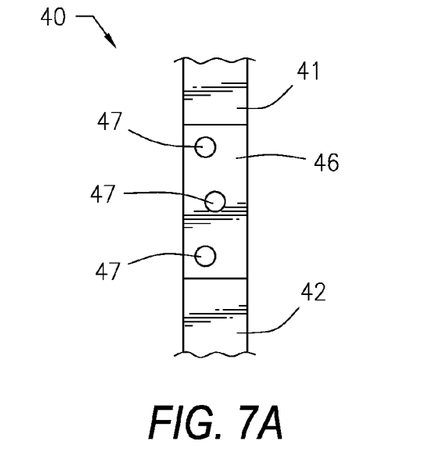
FIG. 7A is a close-up side view of the inside of the hinge assembly.
Figure 7B:
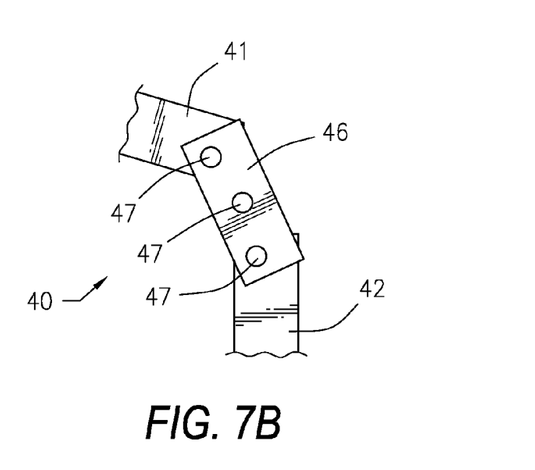
FIG. 7B is a close-up side view of the inside of the hinge assembly in a bent position.

The bar and rod assembly 30 may include further elements to allow the bar and rod assembly 30 to bend at the user's knee 6 for greater ease of use. For example, each of the bars 31 may have a hinge assembly 40. The outside of the hinge assembly is shown in FIGS. 6A and 6B, while the inside is shown in 7A and 7B. Each bar 31 may comprise an upper bar 41, a lower bar 42, and a middle piece 43 between the upper bar 41 and the lower bar 42. The upper bar 42 may have a rounded corner 44 adjacent the middle piece 43, and the middle piece 43 may have a rounded corner 45 adjacent the lower bar 42. The upper bar 41, middle piece 43, and lower bar 42 may be connected via a connector plate 46. The upper bar 41, middle piece 43, and lower bar 42 may be pivotally connected to the connector plate 46 via attachment devices 47, such as screws or bolts. The rod 35 may comprise an upper rod 48, a lower rod 49, and a spring 50 connecting the upper rod 48 to the lower rod 49. Likewise, a spring 51 may be attached to the upper bar 41 at one end and the lower bar 42 on the other end on the bar 31 opposite the bar 31 adjacent the rod 35. The foregoing elements may allow the bars 31 to bend, as shown in FIGS. 3, 6B, and 7B.

The pivot points of the hinge assembly 40 may facilitate the arch bend of the user's knee. The center pivot point may be forward of the other two pivot points to allow the arch movement of middle piece 43 in relation to upper bar 41 and lower bar 42. The eccentric knee bend of the leg support 1 may allow constant pressure in all planes of movement.

The flat surfaces of the upper bar 41, lower bar 42, and middle piece 43, combined with the spring 51, may allow for a locking position of the hinge assembly 40. Spring tension at the knee may create pressure that makes the hinge assembly 40 return to a straight, upright position and remain locked straight until sufficient pressure is applied to override the inherent tendency of the hinge assembly 40 to remain straight.

Whereas, the devices and methods have been described in relation to the drawings and claims, it should be understood that other and further modifications, apart from those shown or suggested herein, may be made within the spirit and scope of this invention.

What is claimed is:

1. A leg support adapted for use on a user's leg, where the leg comprises an upper leg, a knee, a lower leg, and a foot, the leg support comprising:

an upper assembly capable of surrounding the user's upper leg, where the upper assembly has an adjustable circumference and where the upper assembly comprises:
  a wrap; and
  a wire assembly comprising a first closure side, a second closure side removably attached to the first closure side, and at least one wire extending between the first closure side and the second closure side, such that the first closure side, the second closure side, and the at least one wire surround the wrap; and
a rod attached to the wire assembly such that moving the rod upward causes the circumference of the upper assembly to decrease, where the rod is sufficiently long to extend from the upper assembly past the user's foot such that when the user takes a step on a walking surface, the rod strikes the walking surface and causes the circumference of the upper assembly to decrease, preventing the user's foot from striking the walking surface or any part of the leg support,
where the rod has at least one channel through which the at least one wire extends and where the upper assembly further comprises two anchor bars, where the anchor bars are attached to the wrap, where the anchor bars each have at least one channel through which the at least one wire extends, and where the rod is located between the two anchor bars with the channels of the rod aligning with the channels of the anchor bars, such that the wire extends through one of the channels in one of the anchor bars, through one of the channels in the rod, then through one of the channels in the other anchor bar.

2. The leg support of claim 1 where the first closure side is attached to the wrap.

3. The leg support of claim 1 where:
the first closure side has a series of posts;
the second closure side has a series of posts;
the wire has a first end and a second end; and
the first end of the wire is attached to the first closure, the wire alternately wraps around the posts of the second closure side and the posts of the first closure side in series, and the second end of the wire is attached to the second closure.

4. The leg support of claim 1 where the wire assembly further comprises a tensioning device.

5. The leg support of claim 1 further comprising two bars attached to the upper assembly and extending downward, where the bars are sufficiently long to extend from the upper assembly past the user's foot but not as long as the rod.

6. The leg support of claim 5 where the bars run along either side of the user's leg, and the rod runs along the outside of the user's leg.

7. The leg support of claim 5 further comprising a cross piece connecting the two bars under, but not touching, the user's foot.

8. The leg support of claim 5 further comprising a strap securing the two bars to the user's lower leg.

9. The leg support of claim 1 where the rod comprises an upper rod, a lower rod, and a spring connecting the upper rod and the lower rod, where the spring is located adjacent the user's knee when the leg support is in use.

10. A leg support adapted for use on a user's leg, where the leg comprises an upper leg, a knee, a lower leg, and a foot, the leg support comprising:
  an upper assembly capable of surrounding the user's upper leg, where the upper assembly has an adjustable circumference, where the upper assembly comprises a wrap and a wire assembly, and where the wrap comprises a front section, a back section, and two side sections, where the two side sections each have a double layer such that a portion of the front section and a portion of the back section fit between the layers of the side sections to form a cylinder with an adjustable circumference; and
  a rod attached to the wire assembly such that moving the rod upward causes the circumference of the upper assembly to decrease, where the rod is sufficiently long to extend from the upper assembly past the user's foot such that when the user takes a step on a walking surface, the rod strikes the walking surface and causes the circumference of the upper assembly to decrease, preventing the user's foot from striking the walking surface or any part of the leg support.

11. A leg support adapted for use on a user's leg, where the leg comprises an upper leg, a knee, a lower leg, and a foot, the leg support comprising:
  an upper assembly capable of surrounding the user's upper leg, where the upper assembly has an adjustable circumference;
  a rod attached to the upper assembly such that moving the rod upward causes the circumference of the upper assembly to decrease, where the rod is sufficiently long to extend from the upper assembly past the user's foot such that when the user takes a step on a walking surface, the rod strikes the walking surface and causes the circumference of the upper assembly to decrease, preventing the user's foot from striking the walking surface or any part of the leg support;
  two bars attached to the upper assembly and extending downward, where the bars are sufficiently long to extend from the upper assembly past the user's foot but not as long as the rod;
  a cross piece connecting the two bars under, but not touching, the user's foot; and
  a flat piece with a top and a bottom, where the top of the flat piece is attached to the rod such that pressing the bottom of the flat piece causes the rod to move upward.

12. The leg support of claim 11 where the flat piece is connected to the cross piece via two u-shaped connectors, where the u-shaped connectors are attached to the flat piece and extend over the cross piece such that the flat piece cannot move substantially laterally but may move vertically relative to the cross piece.

13. The leg support of claim 12 where the bars each comprise an upper bar, a lower bar, and a middle piece located between the upper bar and lower bar, where the middle piece is located adjacent the user's knee when the leg support is in use.

14. The leg support of claim 13 where each of the bars further comprises a connector plate pivotally connected to the upper bar, the lower bar, and the middle piece such that bar hinges during use.

* * * * *